US009168176B2

(12) United States Patent
Peebles (10) Patent No.: US 9,168,176 B2
(45) Date of Patent: Oct. 27, 2015

(54) COMBINATION EAR AND EYE PROTECTION SYSTEM AND RELATED METHOD

(76) Inventor: Donald Scott Peebles, Bradenton, FL (US)

( * ) Notice: Subject to any disclaimer, the term of this patent is extended or adjusted under 35 U.S.C. 154(b) by 610 days.

(21) Appl. No.: 13/479,529

(22) Filed: May 24, 2012

(65) Prior Publication Data

US 2013/0047322 A1 Feb. 28, 2013

Related U.S. Application Data

(63) Continuation-in-part of application No. 13/217,035, filed on Aug. 24, 2011, now Pat. No. 8,621,664.

(51) Int. Cl.
| | |
|---|---|
| *A61F 9/02* | (2006.01) |
| *A61F 11/14* | (2006.01) |
| *A63B 71/10* | (2006.01) |
| *G02C 3/00* | (2006.01) |
| *G02C 11/00* | (2006.01) |

(52) U.S. Cl.
CPC .................. *A61F 9/029* (2013.01); *A61F 11/14* (2013.01); *A63B 71/10* (2013.01); *G02C 3/003* (2013.01); *G02C 11/10* (2013.01); *A61F 2210/009* (2013.01)

(58) Field of Classification Search
CPC ........ A42B 1/247; A42B 3/042; A42B 3/185; A42B 3/221; G02C 3/02; G02C 3/003; A61F 9/027; A61F 9/029; A61F 11/14
USPC ............ 2/10, 209, 209.13, 422, 423; 351/158
See application file for complete search history.

(56) References Cited

U.S. PATENT DOCUMENTS

| | | | | | |
|---|---|---|---|---|---|
| 2,502,162 | A | * | 3/1950 | Malcom | 2/453 |
| 3,237,203 | A | * | 3/1966 | Nielsen | 2/10 |
| 4,802,243 | A | * | 2/1989 | Griffiths | 2/422 |
| 4,856,089 | A | * | 8/1989 | Horton | 455/351 |
| 5,133,596 | A | * | 7/1992 | Korny et al. | 351/158 |
| 5,179,736 | A | * | 1/1993 | Scanlon | 2/209 |
| 5,278,999 | A | * | 1/1994 | Brown et al. | 2/209 |
| 5,323,493 | A | * | 6/1994 | Ogiba | 2/422 |
| 5,719,655 | A | * | 2/1998 | Peschel et al. | 351/111 |
| 5,724,119 | A | * | 3/1998 | Leight | 351/158 |
| D404,174 | S | * | 1/1999 | Childs et al. | D29/112 |
| 6,481,846 | B1 | * | 11/2002 | Mikysa | 351/158 |
| 6,511,177 | B1 | * | 1/2003 | Hall et al. | 351/158 |
| 7,020,901 | B2 | * | 4/2006 | Brhel | 2/209 |
| 7,020,903 | B2 | * | 4/2006 | Artzberger | 2/431 |
| 8,555,423 | B2 | * | 10/2013 | Giroux et al. | 2/422 |
| 2006/0152671 | A1 | * | 7/2006 | Risso et al. | 351/155 |
| 2009/0284712 | A1 | * | 11/2009 | Brooks | 351/155 |
| 2011/0209273 | A1 | * | 9/2011 | Fountain et al. | 2/423 |
| 2012/0272484 | A1 | * | 11/2012 | Willborn | 24/3.11 |
| 2012/0297522 | A1 | * | 11/2012 | Treger et al. | 2/209.13 |

* cited by examiner

*Primary Examiner* — Amy Vanatta
(74) *Attorney, Agent, or Firm* — Allen Dyer Doppelt Milbrath & Gilchrist (57) ABSTRACT

A combination headgear and eyewear system including eyewear that magnetically attaches to the headgear. A magnetic ball and disc joint allows the eyewear to pivot on the headgear and into a position wherein the eyewear rests upon a user's face. Adjustable temples allow the eyewear to be configured so to accommodate a large range of head sizes.

22 Claims, 9 Drawing Sheets

COMBINATION EAR AND EYE PROTECTION SYSTEM AND RELATED METHOD

CROSS-REFERENCE TO RELATED APPLICATION

This Continuation-in-Part application is a continuation of U.S. patent application Ser. No. 13/217,035 filed on Aug. 24, 2011 now U.S. Pat. No. 8,621,664 entitled "Combination Headgear and Eye Protection System," the contents of which are incorporated by reference herein.

FIELD OF THE INVENTION

This invention is directed to a combination headgear and eye protection system. More specifically, the technology relates to adjustable eye protection that attaches to headgear using magnetic means, a kit for user assembly of an eye protection system that attaches to headgear using magnetic means, and related methods.

BACKGROUND OF THE INVENTION

In certain industrial professions and sporting activities, it is desirable to wear headgear to protect the participant's hearing from noise having a potentially dangerous sound pressure level. Examples in the professional setting include, without limitation, construction workers, craftsman, airport ground support, and military personnel. Sportsmen who often encounter loud noises include hunters and any individuals who recreationally use firearms. These individuals must don earplugs, ear muffs, or similar headgear in order to prevent hearing loss or injury to the user's hearing.

In addition, these users often opt to use some form of protective eyewear in conjunction with headgear. For example, there is often a risk of eye damage in the event of eye contact with an errantly ejected shell from a firearm. Likewise, there is often a risk of eye contact with debris when the user is engaged in a professional activity such as construction, woodworking, or use of heavy machinery.

Numerous difficulties are encountered when a user opts to wear both eyewear and headgear simultaneously. First, it is often cumbersome and uncomfortable to fit eyewear in combination with the headgear. Second, it remains difficult for the user to remove and later reposition the eyewear when the user must insert a portion of the eyewear within the headgear. Lastly, eyewear worn underneath hearing protection may compromise the seal between ear protection and the user's ears, rendering the protection less efficacious.

Accordingly, there is a need in the art for headgear and safety gear that allows eyewear to be quickly and easily secured to headgear, when the headgear is already worn by the user. Moreover, there is a further need for a system that allows the eyewear to be quickly removed and stowed when the user does not need the eyewear during a professional or recreational sporting event.

SUMMARY OF THE INVENTION

This invention solves some of the current limitations in the art of headgear assemblies and eyewear systems. In particular, the present invention allows a user to rapidly and magnetically attach and remove eyewear to headgear (such as safety ear cups that reduce noise heard by the user). The present invention contemplates a system comprising headgear for a user to don that ultimately attaches to a lens for protecting the user's eyes. Two temples communicate with the lens, each temple having a distal terminus that attaches to a first attachment means on each temple. A second attachment means is on the headgear, being for magnetically attaching to the first attachment means for removably attaching the headgear to the temples. The first attachment means is shaped to be at least one of a ball, ball socket, and disc, while the second attachment means is also shaped to be at least one of a ball, ball socket, and disc. The first attachment means is made from at least one of a magnetic material and a ferrous material, and the second attachment means is also made from at least one of a magnetic material and a ferrous material.

In another embodiment, a magnetic ball-and-disc joint is situated between each terminus of the two temples and the headgear, the joint forming a magnetically attachable and articulable junction between the two temples and the headgear.

The ear cups comprise a headband for positioning the headgear on the user's head, the headband having a first end and a second end. A first ear cup is attached to the first end of the headband and a second ear cup is attached to the second end of the headband. A first yoke attaches the first ear cup to the first end of the headband, and a second yoke attaches the second ear cup to the second end of the headband.

The headgear is at least one of a stereo headphone, radio earphone, 2-way communication headphone, and a hardhat/ear cup combination unit. The second attachment means is positioned on the cup of the safety earmuff, the inside the cup of the safety earmuff, or the yoke of the safety earmuff.

The lens of the eyewear is at least one a safety lens, sunglass lens, prescription lens, prescription sunglass lens, prescription safety lens, and sunglass safety lens.

Additionally, the invention contemplates an eyewear assembly kit comprising safety goggles having adjustable temples, a first attachment portion attached to each of the temples, a second attachment portion for magnetic attachment to the first attachment portion, adhesive for adhering the second attachment portion to headgear, and instructions for assembling the safety goggles, the second attachment portion, and the adhesive into a eyewear assembly.

BRIEF DESCRIPTION OF THE DRAWINGS

For a fuller understanding of the invention, reference is made to the following detailed description, taken in connection with the accompanying drawings illustrating various embodiments of the present invention, in which.

DETAILED DESCRIPTION OF THE INVENTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
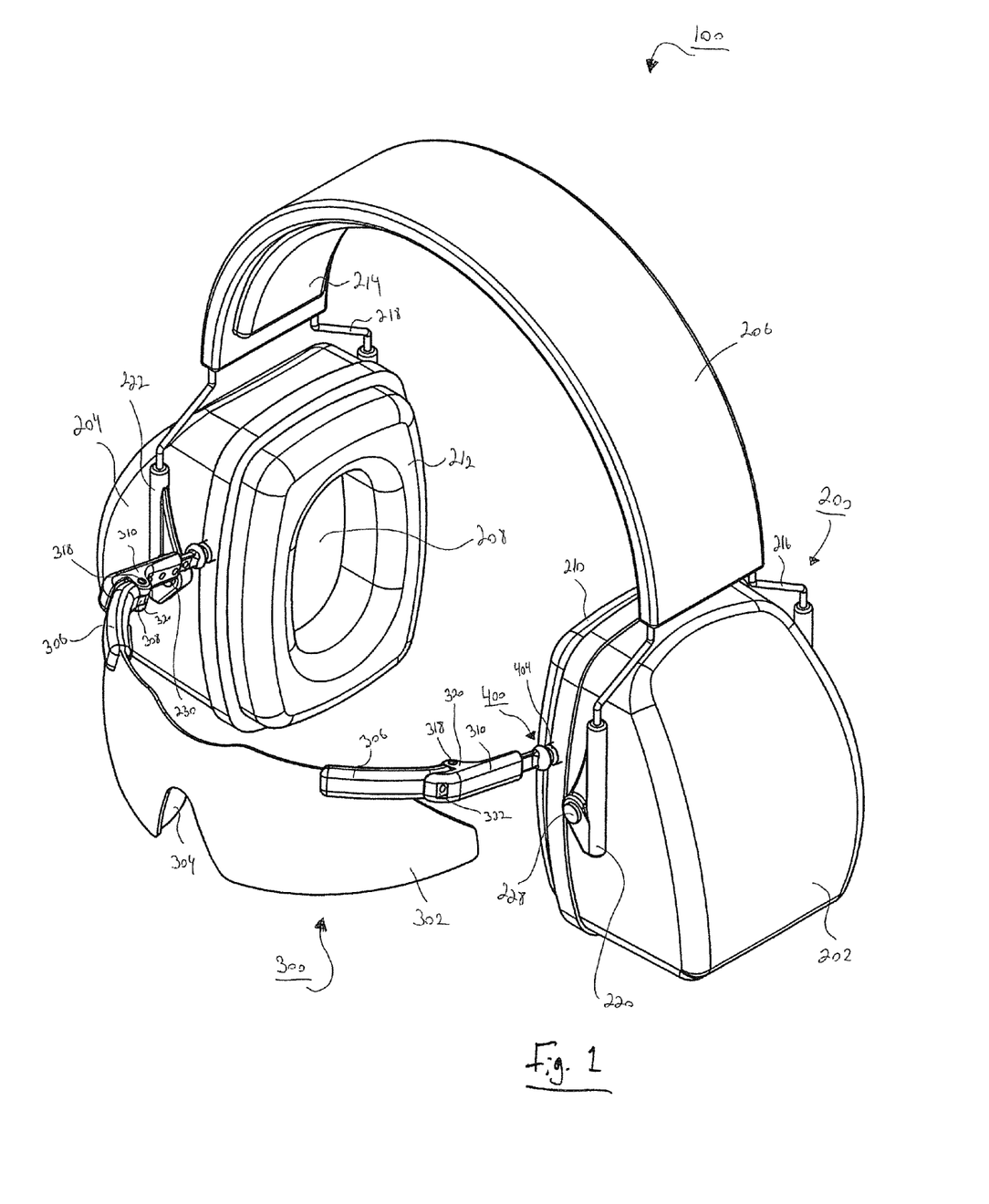
FIG. 1 is a perspective view illustrating headgear to which eyewear is magnetically attached.
Figure 2:
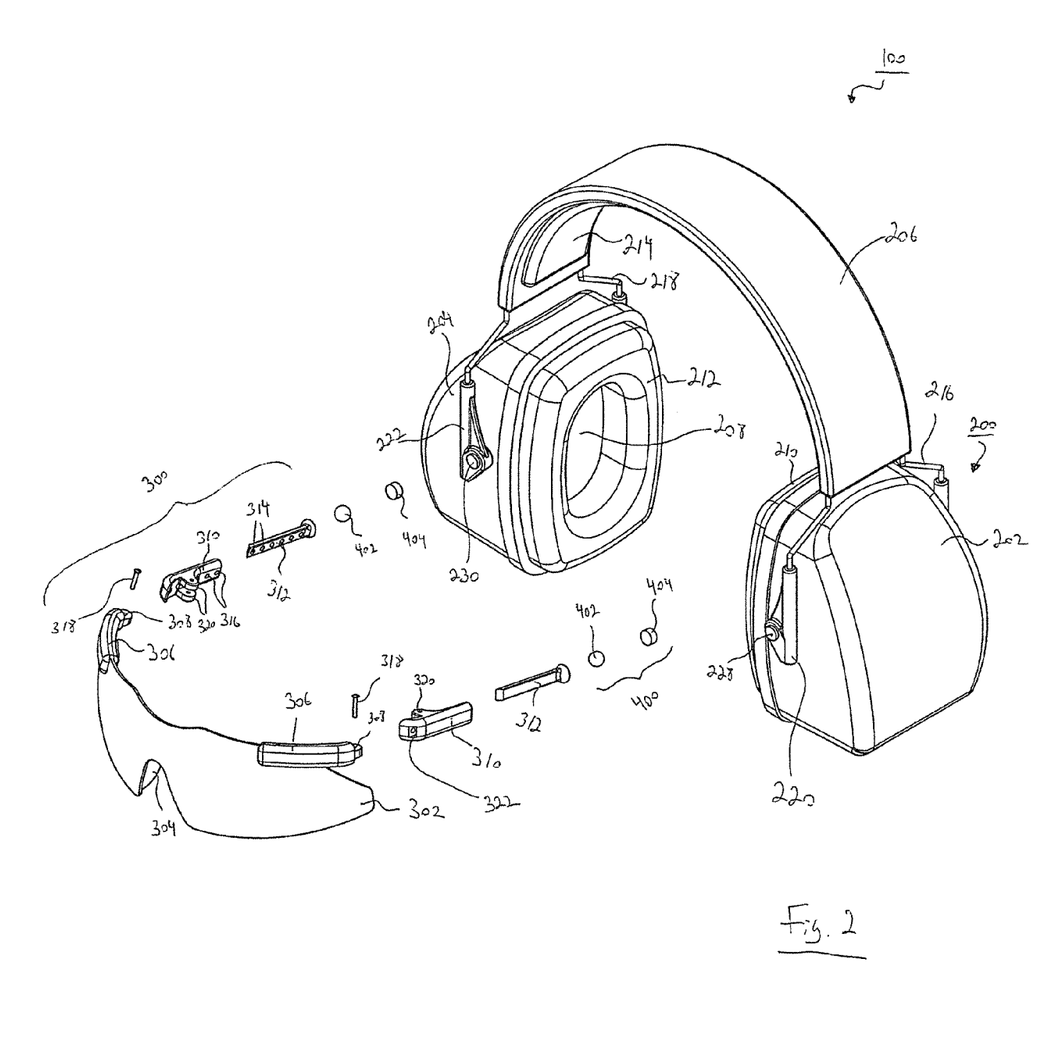
FIG. 2 is an exploded perspective view of the system illustrated in FIG. 1.

FIGS. 1 and 2 illustrate, by way of example, the overall components of the system 100. As shown, there are three primary components of the system 100: the headgear 200, the eyewear 300, and the magnetic attachment means 400 (that connects to the headgear 200 to the eyewear 300).

Headgear

As shown in both FIG. 1 and FIG. 2, the headgear 200 includes three main parts: a first ear cup 202, a second ear cup 204, and an adjustable headrest 206. As shown in FIG. 1, the adjustable headrest 206 connects to both the first ear cup 202 and second ear cup 204. Preferably, the ear cups 202, 204 are made out of a lightweight, resilient, and sound reducing material such as a plastic, composite, polymer, or metal. Moreover, the inner portion of both ear cups 202, 204 may be lined with sound reducing material 208.

In alternate embodiments, the headgear 200 headgear is at least one of stereo headphones, radio earphones, 2-way communication headphones, and hardhat/ear cup combination units.

Both ear cups 202, 204 are circular or elliptical in cross section, having a sufficient size and dimension to cover a user's ears. The ear cups 202, 204 each include a soft and pliant cushion 210, 212. The cushions 210, 212 allow the headgear 200 to comfortably sit about the user's head without excessive pressure and also provide a seal to reduce the sound pressure level the user experiences when wearing the headgear 200. While numerous materials are contemplated for the cushions 210, 212, they are preferably made of rubber, neoprene, plastic, textile or like material. However, other similarly lightweight and resilient materials, known to those skilled in the art, may be used.

With continuing reference to FIGS. 1 and 2, by way of example, the salient components of the adjustable headrest 206 are illustrated. As shown, the adjustable headrest 206 includes a head cushion 214, first yokes 216 and corresponding second yokes 218. The first yokes 216 connect to the first ear cup 202, and the second yokes 218 connect to the second ear cup 204. In one embodiment, the yokes 216, 218 each slidingly engage respective yoke housings 220, 222 that are attached to the first and second ear cups 202, 204, respectively.

The first yoke housings 220 are rotatably attached to a first outer wall 224 of the first ear cup 202, preferably through the use of first pivot pins 228. Correspondingly, the second yoke housings 222 are rotatably attached to a second outer wall 226 of the second ear cup 204, preferably through the use of second pivot pins 230. The pivot pins 228, 230 create a joint to which the adjustable headrest 206 and yokes 216, 218 attach to the ear cups 202, 204 so as to allow a comfortable, adjustable, and custom fit about the user's head.

Figure 3:
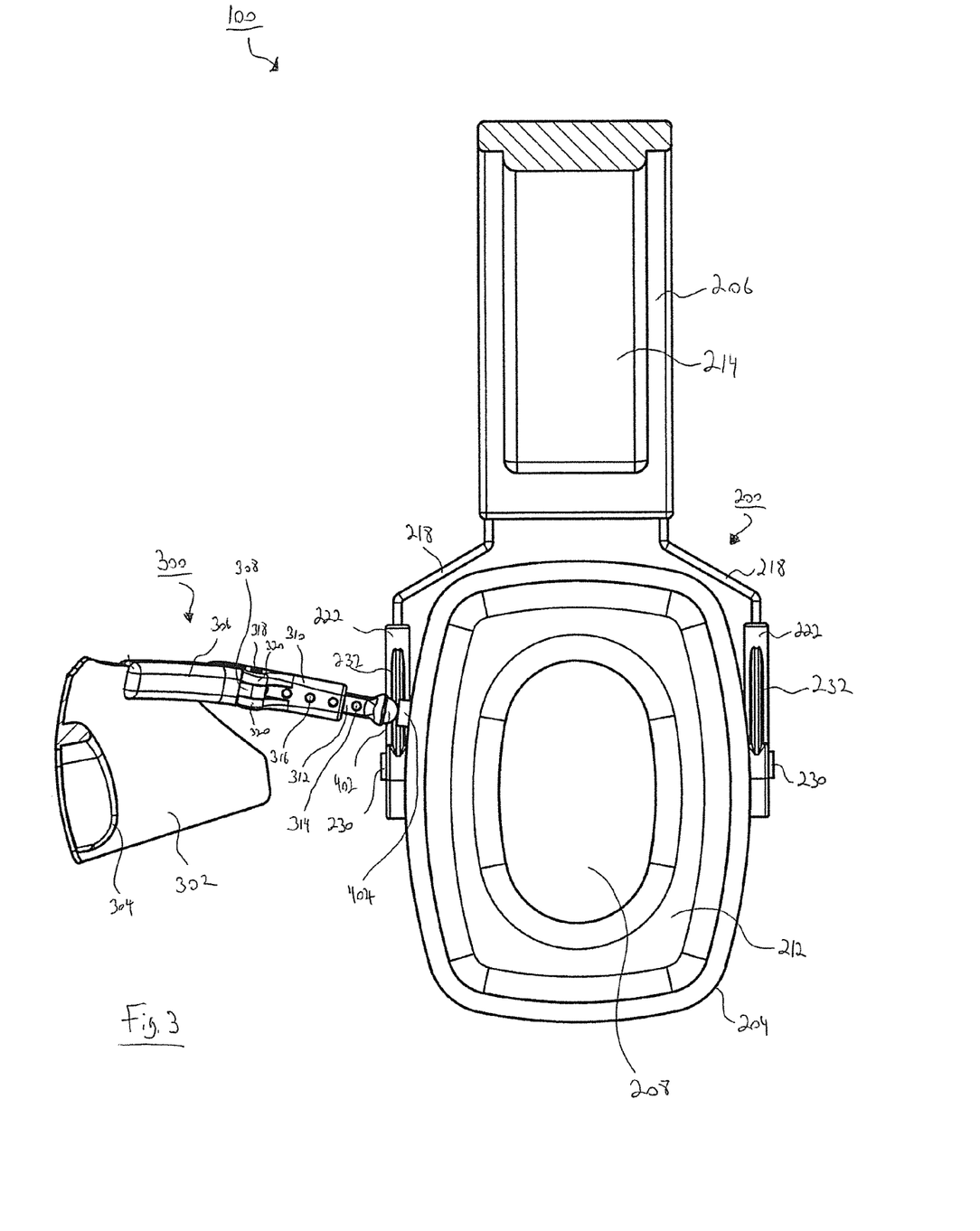
FIG. 3 is a side view of the system illustrated in FIGS. 1 and 2.

Referring to FIG. 3, it is illustrated that the yokes 216, 218 slidingly engage hollow cavities 232 of their respective yoke housings 220, 222, thus allowing a user to adjust the height between the ear cups 204, 204 and the headrest 206. In another embodiment, the yokes 216, 218 communicate directly with the ear cups 202, 204 and are pivotally attached with pivot pins 228, 230.

Protective Eyewear

FIGS. 1 and 2 illustrate, by way of example, the components of representative eyewear 300. The eyewear 300 comprises a lens 302 made from a hard glass or polymer that functions as a shield. In a preferred embodiment, the lens 302 is constructed from high impact polycarbonate. The lens 302 depicted in the illustrations is a single lens 302 with an integral nose pad 304, but a conventional dual lens eyeglass construction held within an eyeglass frame is also contemplated. The lens 302 (or lenses) comprises at least one of an anti-fog coating, UV resistant material, prescription corrective lenses, bifocal lenses, magnifying lenses, shaded lenses, polarized lenses, safety lenses, and combinations thereof.

The lens 302 is engaged by at least one frame member 306, the primary purpose of which is to provide a hinged attachment means 308 for temples 310. Each temple 310 comprises a hollow passageway 322 that travels through the length of the temple 310 that serves to maintain a projection 312 that extends from the temples 310 so to communicate with the headgear 200 using the magnetic attachment means 400. The projections 312 are telescoping members that provide a means to adjust the distance the lens 302 and nose pad 304 are from the headgear 200 to effectuate a proper fit for the user.

In the embodiment illustrated by FIG. 2, the projection 312 comprises a plurality of detents 314. A detent 314 engages at least one cavity 316 in the temples 310 for the purpose of arresting the projection 312 at a desired point. This allows a user to adjust the distance the projection 312 protrudes from the temple 310 passageway 322. The angle between the lens 302 and the temples 310 (and therefore the projection 312 also) is adjustable since the temples 310 are hingedly attached to the hinged attachment means 308 by a hinge pin 318 that engages both the frame's 306 hinged attachment means 308 and a temple hinge portion 320.

In one embodiment, the projection 312 telescopes through the entire length of the temple passageway 322 and protrudes outward through the entirety of the temple 310. This allows the projection to have a greater number of points where detents 314 can engage cavities 316 so that a greater adjustment range of the projections 312 is possible. This additional range, allows protrusion of the projections 312 forward of the hinge pin 318, and due to the size of the ear cups 202, 204 there is limited available space between the cups 202, 204 and the lens 302 area of the eyewear. This is especially true of persons with relatively short "ear-to-front-of-face" dimensions. For persons with such dimensions, the excess length of the projections 312 can be trimmed off once the person determines the excess length of the projection 312 is not needed. This feature allows for longer projections 312 which in turn will provide greater adjustability of the eyewear 300 to enable fitting a broader range of users.

Magnetic Connectors

FIGS. 1 and 2 illustrate, by way of example, the components of the magnetic connectors 400. First turning to FIG. 2, a first magnetic connector 402 is affixed to a projection 312. Likewise, a second magnetic connector 404 is affixed to the headpiece 200. As shown, it is preferable that the first magnetic connector 402 is a ball and the second magnetic connector 404 is a disc. If the first connector 402 is a magnet, the second connector 404 is either a magnet or made from a ferrous material. If the second connector 404 is a magnet, the first connector 402 is either a magnet or made from a ferrous material. In a preferred embodiment, the ferrous material is steel. The first connector 402 is press-fit into or adhered to the projection 312.

Figure 4:
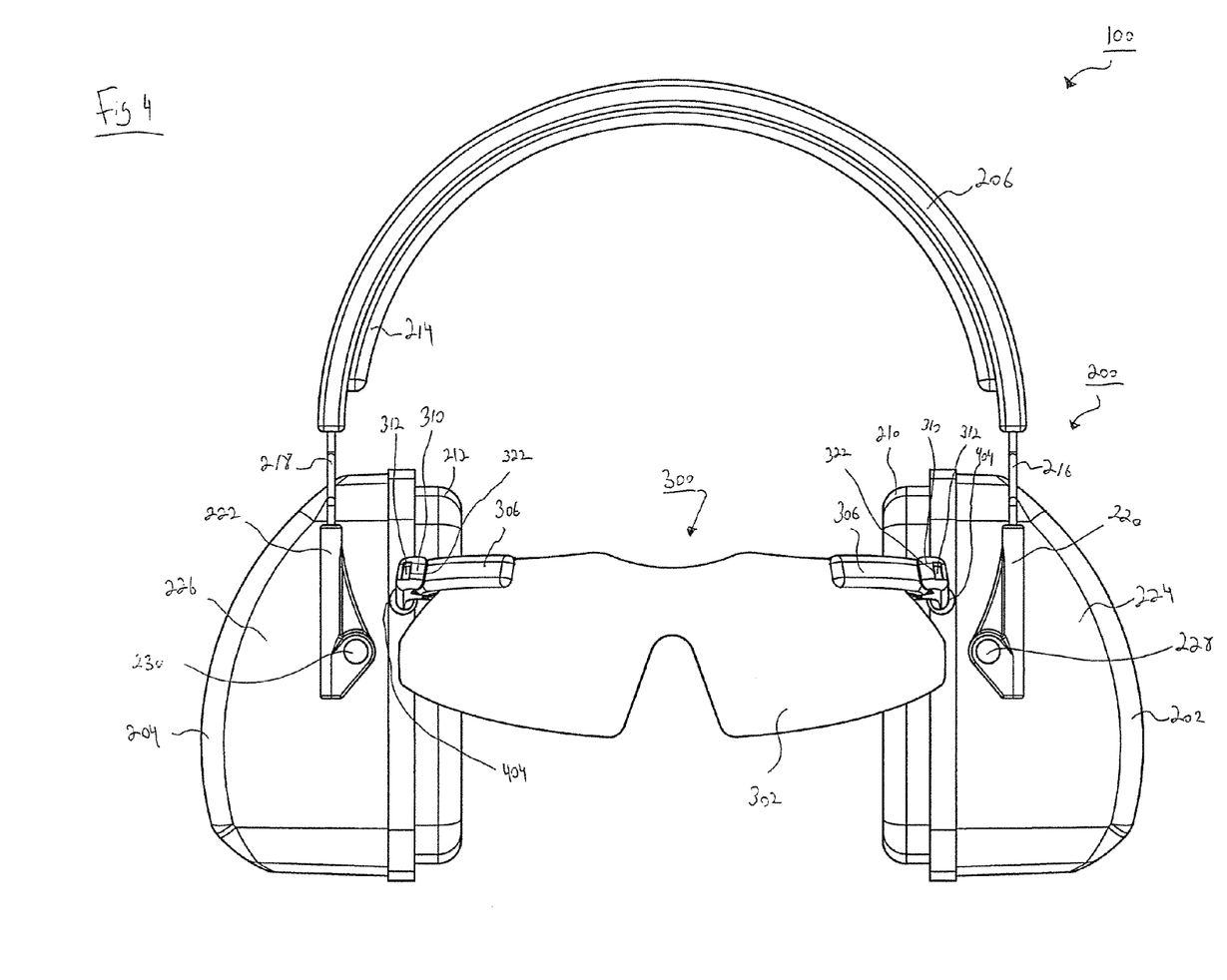
FIG. 4 is a front view of the system illustrated in FIG. 1-3.
Figure 5:
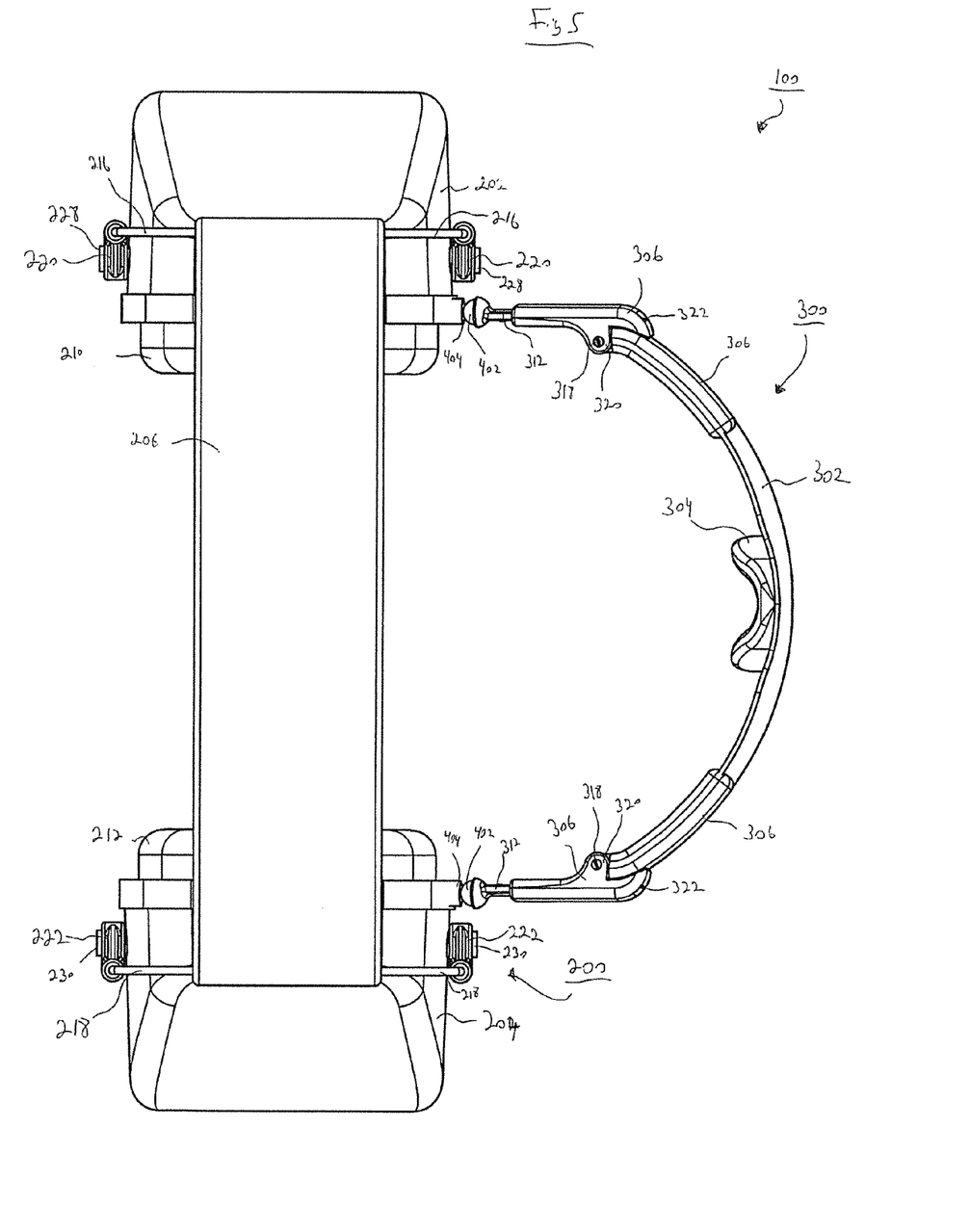
FIG. 5 is a top view of the system illustrated in FIG. 1-4.

FIGS. 4 and 5 are alternate views of FIGS. 1 and 3, and are included for clarity.

Alternate Embodiments

Figure 6:
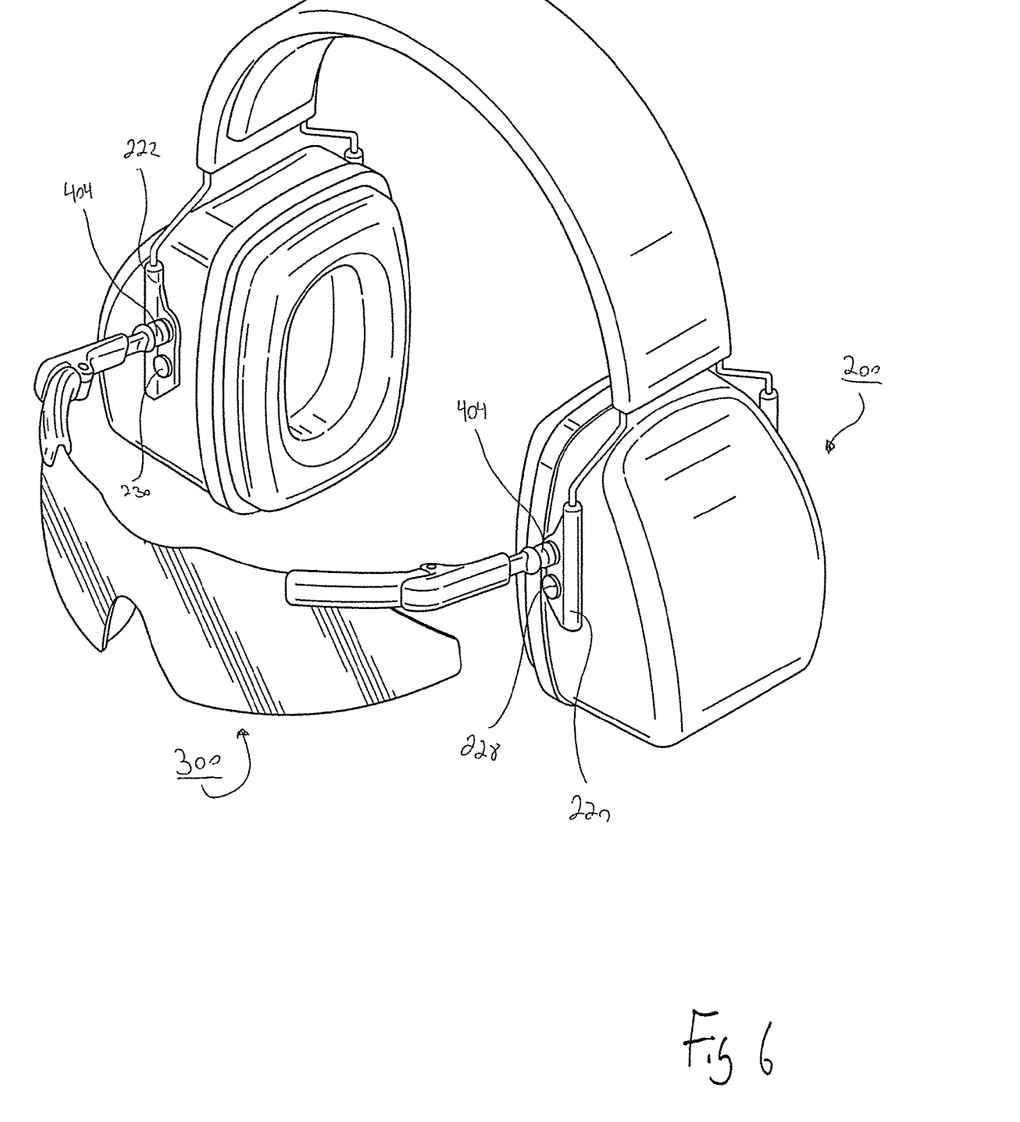
FIG. 6 is a perspective view illustrating an alternate embodiment of the invention.
Figure 7:
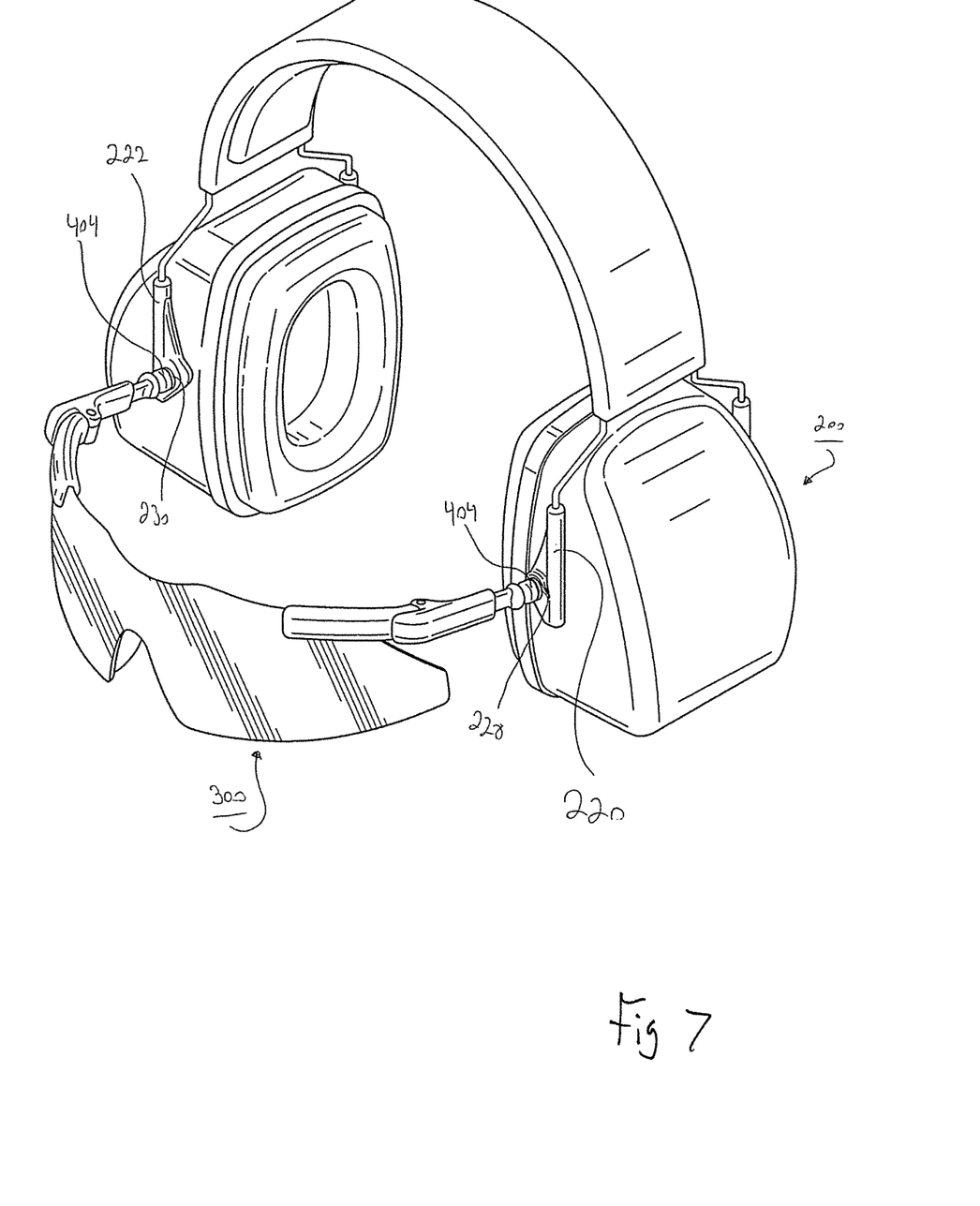
FIG. 7 is a perspective view illustrating another alternate embodiment of the invention.
Figure 8:
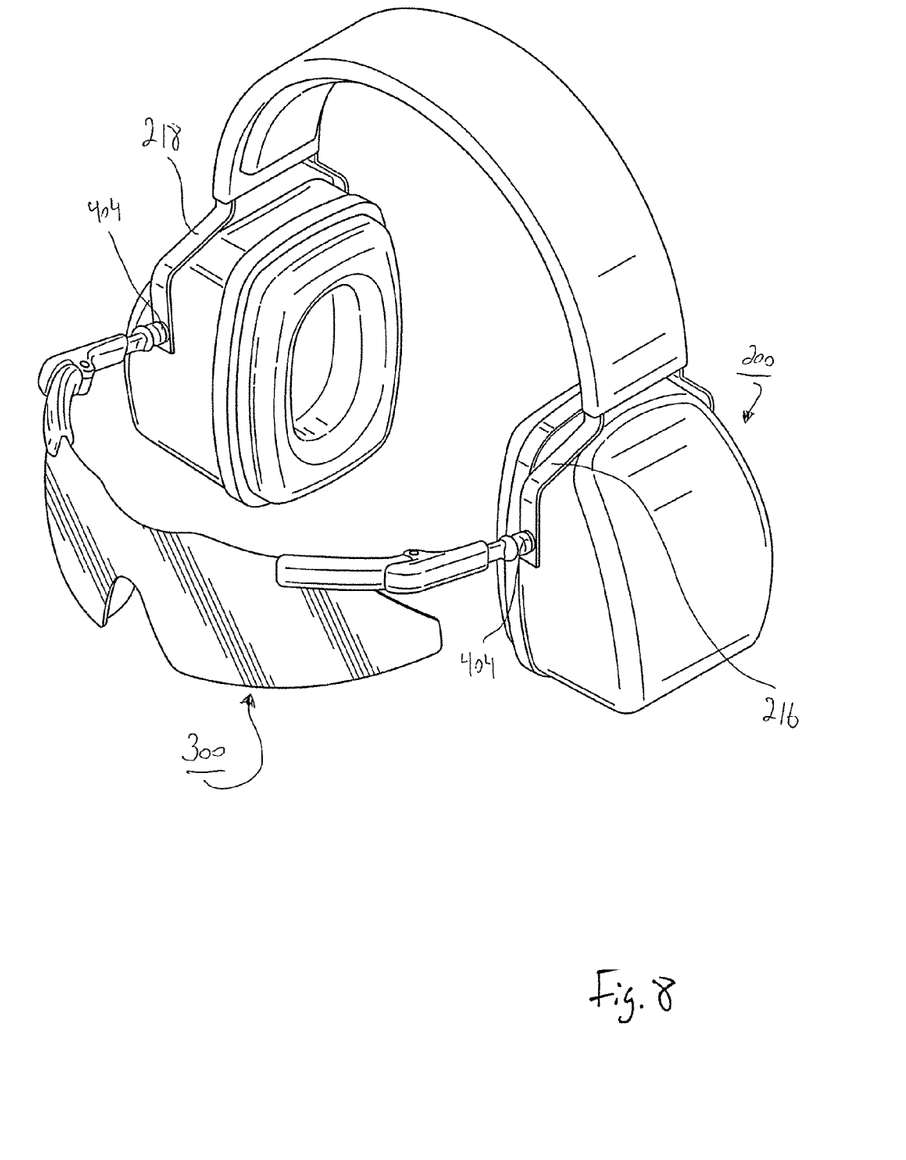
FIG. 8 is a perspective view illustrating yet another alternate embodiment of the invention.

As further shown in FIGS. 1 and 2, connectors 402, 404 are arranged as a magnetic ball-and-disc device. Here, each disc 404 is permanently affixed to an ear cup 202, 204. In another embodiment as illustrated by FIG. 6, each second connector 404 is affixed to a yoke housing 220, 222. In another embodiment as illustrated by FIG. 7, each second connector 404 is affixed to a pivot pin 228, 230. In yet another alternate embodiment, as illustrated by FIG. 8, each second connector 404 is affixed to a yoke 216, 218. In these embodiments of FIGS. 1, 6, 7, and 8, the eyewear 300 can be easily affixed to the headgear 200 through the magnetic connectors 400. Likewise, the eyewear 300 can be quickly removed when not in use via the magnetic connectors 400. The second connectors 404 may, in another embodiment, be installed inside each ear cup 202, 204. In this embodiment, the magnetic forces involved are strong enough to penetrate the ear cup 202, 204 material and effectuate a strong connection between the ear cups 202, 204 and the first connectors 402.

Magnetic Eyewear Attachment Kit

Figure 9:
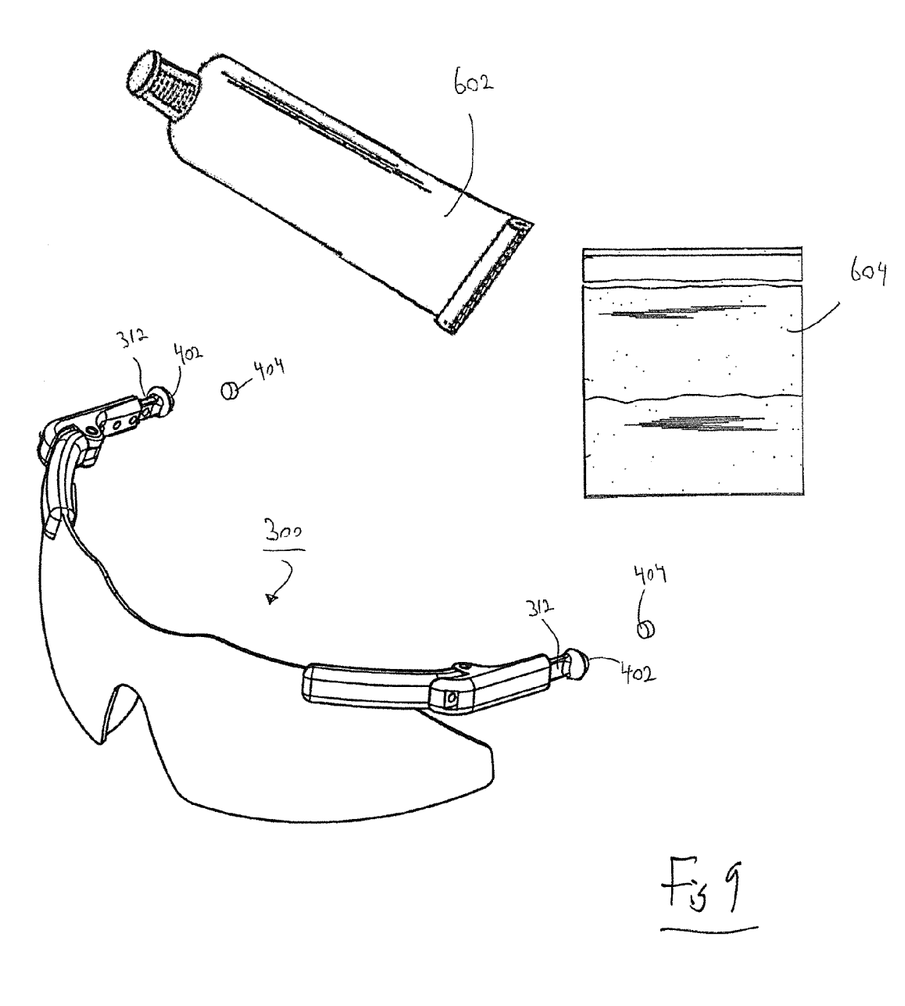
FIG. 9 illustrates a magnetic eyewear attachment kit.

The invention contemplates, as illustrated in FIG. 9, a kit 600 having eyewear 300 as described herein having a first connector 402 attached to each projection 312. Additionally, the kit 600 comprises adhesive 602, second connectors 404, and instructions 604 indicating how to use the kit 600. The kit 600 provides that a user attaches second connectors 404 to a user's existing headgear 200. The instructions 604 instruct the user to apply adhesive 602 to attach the second connectors 404 to headgear 200. The adhesive 602 is liquid or a film. This allows the user to adapt headgear 200 of the user's choice to be magnetically attachable to the eyewear 300 in the kit. For example, the user's headgear 200 can be earmuffs, stereo headphones, radio earphones, 2-way communication headphones, or hardhat/ear cup combination units. The instructions 604 are provided on paper or using electronic media.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which I claim:

1. A combination headgear and eyewear system comprising:
   headgear for a user to don;
   a lens to protect the user's eyes;
   two spaced temples coupled with the lens, each temple having a distal terminus;
   first attachment means oriented rearwardly on each terminus of the two temples; and
   second attachment means oriented forwardly on the headgear, the second attachment means magnetically attached to each of the first attachment means for removably attaching the headgear to both temples.

2. The combination headgear and eyewear system of claim 1, further comprising a frame member attaching the two temples to the lens.

3. The combination headgear and eyewear system of claim 1, wherein the headgear comprises spaced ear cups for reducing noise levels.

4. The combination headgear and eyewear system of claim 2, wherein the headgear comprises:
   a headband for positioning the headgear on the user's head, the headband having a first end and a second end; and
   a first ear cup attached to the first end of the headband;
   a second ear cup attached to the second end of the headband.

5. The combination headgear and eyewear system of claim 4, further comprising:
   a first yoke attaching the first ear cup to the first end of the headband; and
   a second yoke attaching the second ear cup to the second end of the headband.

6. The combination headgear and eyewear system of claim 1, wherein:
   the first attachment means is shaped to be at least one of a ball, ball socket, and disc; and
   the second attachment means is shaped to be at least one of a ball, ball socket, and disc.

7. The combination headgear and eyewear system of claim 1, wherein:
   the first attachment means is made from at least one of a magnetic material and a ferrous material; and
   the second attachment means is made from at least one of a magnetic material and a ferrous material.

8. The combination headgear and eyewear system of claim 3, wherein the second attachment means is positioned on each of the spaced ear cups of the headgear.

9. The combination headgear and eyewear system of claim 3, wherein the second attachment means is positioned inside each of the spaced ear cups of the headgear.

10. The combination headgear and eyewear system of claim 5, wherein the second attachment means is positioned on each of the first and second yokes of the headgear.

11. The combination headgear and eyewear system of claim 1, wherein the headgear is at least one of a stereo headphone, radio earphone, 2-way communication headphone, and a hardhat/ear cup combination unit.

12. The combination headgear and eyewear system of claim 1, wherein the lens is at least one of a safety lens, sunglass lens, prescription lens, prescription sunglass lens, prescription safety lens, and sunglass safety lens.

13. A combination headgear and eyewear system comprising:
   headgear for a user to don;
   a lens to protect the user's eyes;
   two spaced temples coupled with the lens, each temple having a rearwardly-oriented distal terminus;
   a magnetic ball-and-disc joint situated between the terminus of each temple and the headgear, the joint forming a magnetically attachable and articulable junction between the rearwardly-oriented distal termini of the two temples and forwardly oriented points on the headgear.

14. The combination headgear and eyewear system of claim 13, wherein at least one frame member attaches the two temples to the lens.

15. The combination headgear and eyewear system of claim 13, wherein the headgear comprises spaced ear cups for reducing noise levels.

16. The combination headgear and eyewear system of claim 15, wherein the headgear comprises:
   a headband for positioning the headgear on the user's head, the headband having a first end and a second end; and
   a first ear cup attached to the first end of the headband;
   a second ear cup attached to the second end of the headband.

17. The combination headgear and eyewear system of claim 16, further comprising:
   a first yoke attaching the first ear cup to the first end of the headband; and
   a second yoke attaching the second ear cup to the second end of the headband.

18. The combination headgear and eyewear system of claim 16, wherein each of the ball-and-disc joints attaches to one of the first and second ear cups of the headgear.

19. The combination headgear and eyewear system of claim 16, wherein a disc of each of the ball-and-disc joints is positioned inside one of the first and second ear cups of the headgear.

20. The combination headgear and eyewear system of claim 17, wherein each of the ball-and-disc joints attaches to one of the first and second yokes of the headgear.

21. The combination headgear and eyewear system of claim 13, wherein the headgear is at least one of stereo headphones, radio earphones, 2-way communication headphones, and hardhat/ear cup combination units.

22. The combination headgear and eyewear system of claim 13, wherein the lens is at least one a safety lens, sunglass lens, prescription lens, prescription sunglass lens, prescription safety lens, and sunglass safety lens.

\* \* \* \* \*